United States Patent
Klopfenstein et al.

(10) Patent No.: US 8,217,552 B2
(45) Date of Patent: Jul. 10, 2012

(54) GENERATOR FOR A PIEZOELECTRIC TRANSDUCER

(75) Inventors: Denis Klopfenstein, Morges (CH); Daniel Baour, Rolle (CH)

(73) Assignee: Tip Top Tips Sàrl, Rolle (CH)

( * ) Notice: Subject to any disclaimer, the term of this patent is extended or adjusted under 35 U.S.C. 154(b) by 303 days.

(21) Appl. No.: 12/724,603

(22) Filed: Mar. 16, 2010

(65) Prior Publication Data
US 2010/0231090 A1    Sep. 16, 2010

(30) Foreign Application Priority Data

Mar. 16, 2009  (EP) .................................. 09155282
Aug. 27, 2009  (EP) .................................. 09168871

(51) Int. Cl.
*H01L 41/09* (2006.01)
(52) U.S. Cl. .................... 310/317; 310/316.03
(58) Field of Classification Search ............. 310/316.03, 310/317
See application file for complete search history.

(56) References Cited

U.S. PATENT DOCUMENTS

| | | | |
|---|---|---|---|
| 5,543,679 A | | 8/1996 | Morino et al. |
| 5,563,464 A | * | 10/1996 | Okubu et al. ............. 310/316.02 |
| 6,211,601 B1 | * | 4/2001 | Obara ........................... 310/317 |
| 7,368,851 B1 | * | 5/2008 | Su ................................. 310/317 |
| 2001/0035698 A1 | | 11/2001 | Nakatsuka et al. |
| 2010/0026139 A1 | * | 2/2010 | Yoshida ....................... 310/317 |

FOREIGN PATENT DOCUMENTS

FR    2 391 001    12/1978

OTHER PUBLICATIONS

European Search Report issued in corresponding application No. EP 09 16 8871, completed Dec. 4, 2009.

* cited by examiner

*Primary Examiner* — Thomas M Dougherty
(74) *Attorney, Agent, or Firm* — Griffin & Szipl, P.C.

(57) ABSTRACT

The generator for a piezoelectric transducer, in particular for a piezoelectric motor for medical or dental applications, comprising two transformers (11A, 11B) each including a primary winding (L1) and a secondary winding (L2), and four switches (19A, 19B, 21A, 21B) driven by an ultrasonic frequency oscillator, two of said four switches (21A, 21B) being designed to connect alternately the secondary of each transformer to the piezoelectric load (5), and the two other switches (19A, 19B) being designed to connect alternately the two primary windings to a power supply (17) so that during a first half cycle, called "the positive half cycle" the primary winding of one of said two transformers is charged with power, while the secondary winding of the other transformer discharges power to the piezoelectric load, and so that during a second half cycle, called "the negative half cycle" the secondary winding of said one transformer discharges power to the piezoelectric load, while the primary winding of the other transformer is charged with power.

6 Claims, 3 Drawing Sheets

GENERATOR FOR A PIEZOELECTRIC TRANSDUCER

This application claims priority from European Patent Application No. 09155282.8 of Mar. 16, 2009 and European Patent Application No. 09168871.3 of Aug. 27, 2009 the entire disclosure of which is incorporated herein by reference.

FIELD OF THE INVENTION

The present invention relates to a generator to power a piezoelectric transducer and particularly such usable in dentistry (in the present application, the expression "piezoelectric transducer" refers to any piezoelectric device that converts an electric signal into another quantity. In particular, it follows from this definition that a piezoelectric motor is an instance of a piezoelectric transducer).

PRIOR ART

It is known that the impedance of a piezoelectric transducer tends to vary considerably according to the operating conditions to which it is subjected. On the one hand, the impedance of a piezoelectric device reaches its minimum for the frequency corresponding to series resonance, and on the other hand, an increase in the mechanical load causes an increase in the impedance. These variations of impedance involve certain problems. Indeed, if the transducer is supplied by a generator of "current source" type, the power delivered to the transducer is proportional to the impedance. The power can thus increase in an uncontrolled way. Thus, if for example the apparatus is used for dental scaling, one is likely to damage the tooth while wanting to remove the calculus. On the other hand, if the transducer is supplied by a generator of "voltage source" type, the power provided decreases according to a hyperbolic law in relation with the increase of the impedance. Thus, when more mechanical work is needed, the generator will provide less power; this is not really ideal. In addition, when no mechanical load is present, the power applied to the transducer increases in an uncontrolled manner which can result in a rupture of the piezoelectric tool.

The patent document FR 2'391'001 proposes a solution to the above problem. The generator for supplying a piezoelectric transducer described in this document comprises a transformer whose primary is excited by an oscillator and whose secondary is connected to supply the transducer. The oscillator itself is supplied in parallel by a generator of constant current (current source) and a generator of voltage (voltage source). Means are provided to block the generator of voltage as long as the impedance of the load remains lower than an adjustable threshold and, on the contrary, to block the generator of current as soon as the impedance of the load exceeds the adjustable threshold.

FIG. 1A, drawn from the above-mentioned document, is a diagram showing the delivered power P according to impedance Z of the transducer, respectively in the case of a minimum power (curve I), of an intermediate power (curve II), and maximum power (curve III). If one considers curve II corresponding to the intermediate power, one sees that as long as impedance Z of the transducer remains lower than the reference threshold Zb, the power P delivered to the transducer increases proportionally with the impedance. If the impedance exceeds the threshold, the generator of constant current is blocked and the generator of voltage is freed. As of this moment, the delivered power decreases according to a hyperbolic law as the impedance grows.

The generator for powering a piezoelectric transducer which has just been described has the disadvantage of providing a maximum power only for a quite precise value of the impedance of the transducer (as revealed by the generally triangular form of curves I and II of FIG. 1A). A goal of the present invention is to provide a generator delivering an appreciably constant power on an interval of variation of the impedance (as illustrated by the generally trapezoidal shape of the first curve of FIG. 1B).

SUMMARY OF THE INVENTION

The present invention achieves this goal by providing a generator for supplying power to a piezoelectric transducer according to the appended claim 1.

BRIEF DESCRIPTION OF THE FIGURES

Other characteristics and advantages of this invention will appear with the reading of the description which will follow, given only as non-limiting example, and made in reference to the annexed drawings in which.

DETAILED DESCRIPTION OF A MODE OF REALIZATION

Figure 2:
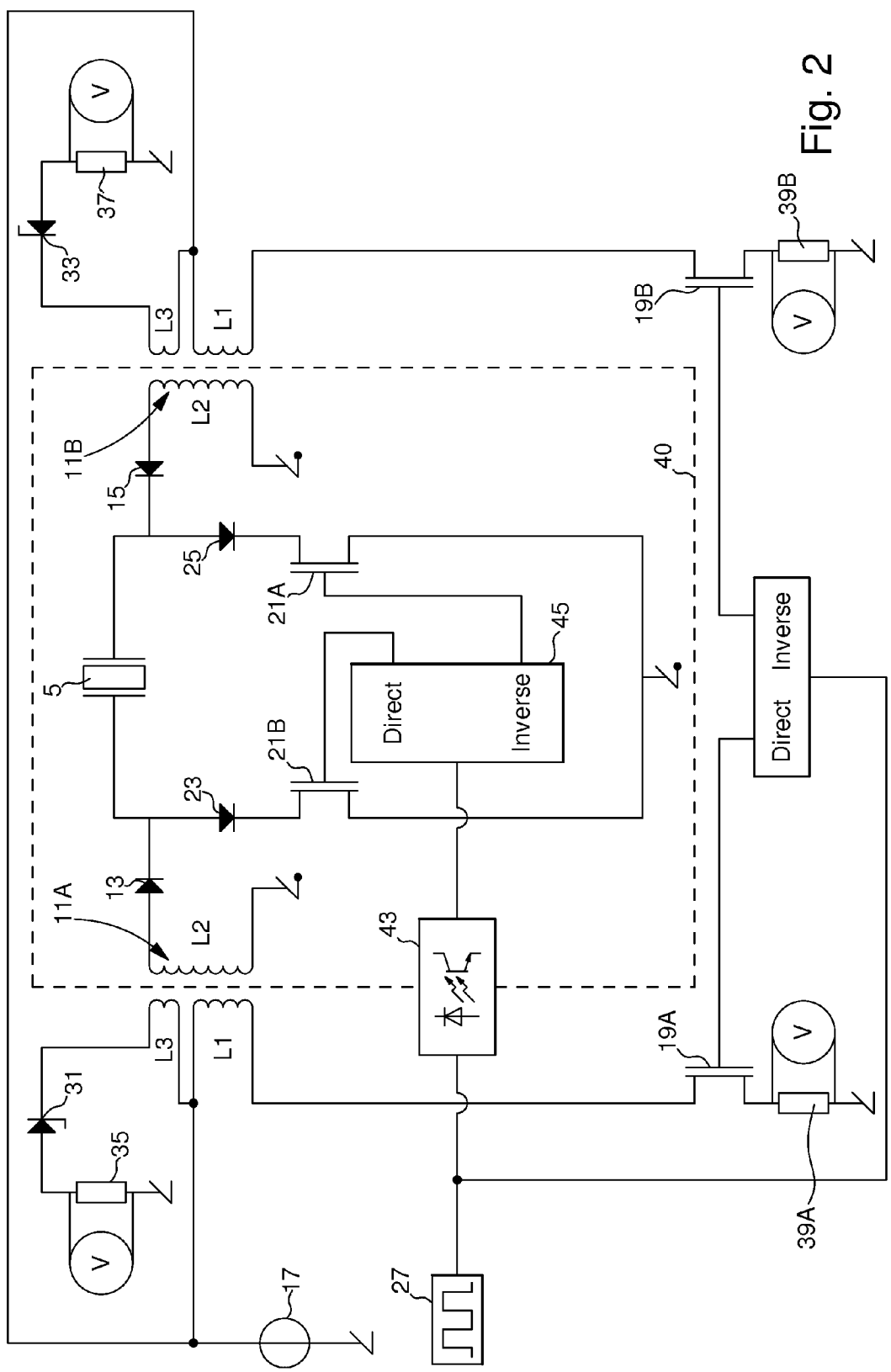
FIG. 2 is an electrical diagram of a particular embodiment of the present invention.

FIG. 2 is an electric diagram of a generator according to a particular embodiment of the invention. The generator for supplying power to the piezoelectric transducer comprises two transformers 11A and 11B, each including a primary winding L1 and a secondary winding L2. Each of the two secondary windings L2 is connected by one of its terminals to one of the poles of the piezoelectric device 5, and by its other terminal to the ground; a diode (13 and 15 respectively) further being inserted between each secondary winding and the piezoelectric device 5.

Each primary winding L1 of transformers 11A and 11B is connected, in series with a switch (19A and 19B respectively), between the terminals of a power supply. In the present example, the power supply is made of a voltage source, referenced 17, of which one terminal is connected to both the primary windings L1 and the other terminal to the ground. The switches 19A and 19B, as well as all the other switches mentioned in present description, are electrically controlled switches that can be implemented in the form of transistors. As well as being connected each to the secondary L2 of one of the two transformers, both poles of the piezoelectric transducer 5 are also connected to the ground via a diode 23 and a switch 21B, respectively via a diode 25 and a switch 21A. This means that on the one hand, the piezoelectric 5 is connected, in series with diode 13, diode 25 and the switch 21A, between the terminals of the secondary L2 of the transformer 11A, and that, on the other hand, the piezoelectric 5 is also connected, in series with diode 15, the diode 23 and the switch 21B, between the terminals of the secondary L2 of the transformer 11B.

Figure 3A:
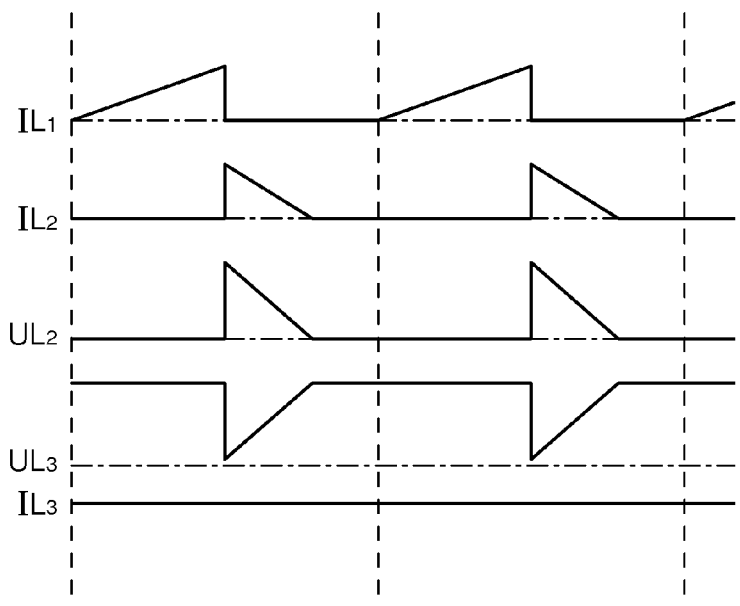
FIGS. 3A, 3B and 3C are three graphs respectively corresponding to three values of the impedance of the piezoelectric transducer and showing the current and the voltage in the windings of the transformers of the generator of FIG. 2.

The switches 19A and 21B, are meant to be driven by a first oscillating control signal, designated here by "direct" signal, while the other switches 19B and 21A are meant to be driven by a second oscillating control signal in opposite phase with the first oscillating signal, hereafter designated as "inverse". In the present example, both control signals are from the same oscillator 27 providing a square voltage made up of a continuing sequence of positive and negative half cylces. During the negative half cycles, the switches 19A and 21B are opened and the switches 19B and 21A are closed. During the positive half cycles, it is the reverse. During negative half cycles, the circuit formed by the secondary L2 of the transformer 11A, the piezoelectric 5, diodes 13 and 25 and the switch 21A is closed and the energy stored in the transformer 11A is transferred to the load. At the same time, the switch 19B is closed and the primary L1 of the transformer 11B is connected directly to the source of voltage 17. The current through the primary produces an increase in the magnetic flux. Energy is thus stored in the magnetic circuit. During the positive half cycle, it is the reverse. The secondary L2 of the transformer 11B gives back its energy while discharging in the circuit including the piezoelectric 5, the diodes 15 and 23 and the switch 21B, while the current through the primary L1 of the transformer 11A stores inductive energy in its magnetic circuit. The graphs of FIG. 3A show the behaviour of the current and of the voltage in winding L1, L2 and L3 of one of the transformers 11A or 11B. It is seen that current IL1 in the primary of the transformer grows regularly during a half cycle before falling to zero and remaining there for the duration of the following half cycle. At the transition between two half cycles, the secondary winding takes over. It is seen that a current IL2, whose intensity is decreasing, circulates in the secondary. In the illustrated example, the current IL2 circulates until complete dissipation of the stored energy. The variations of the voltage UL2 between the terminals of the secondary winding mimic those of the intensity of IL2.

It will be understood that the fact of having two transformers 11A and 11B and alternatively to connect the piezoelectric 5 to one transformer and then to the other, allows to supply the piezoelectric with an alternative voltage. In addition, the skilled person in the art will appreciate, that in short, the function of the switches 19A, 19B, 21A, 21B is to drive the transformers 11A and 11B to make them function in the commonly called "flyback" mode.

Figure 3B:
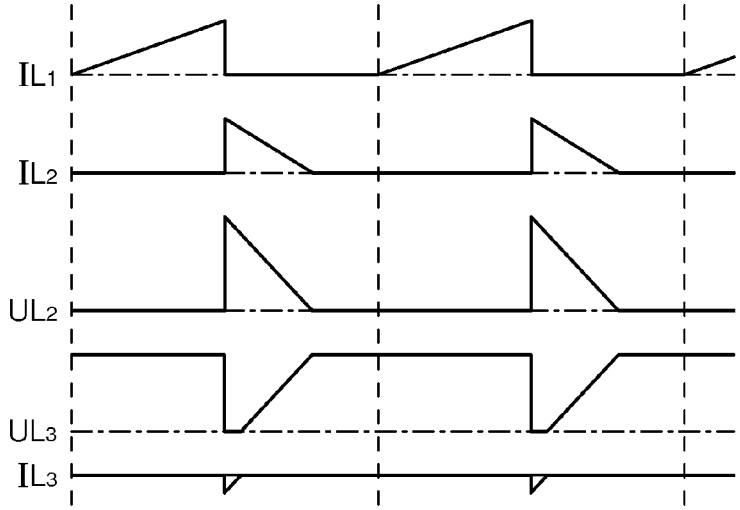

One further sees on FIG. 2 that two resistances (referred respectively 39A and 39B) are connected in series with primary windings L1 and the switches 19A and 19B. The resistances 39A and 39B are respectively provided to allow for measuring the intensity of the current circulating in the primary L1 of the transformers 11A and 11B. The measurement of the current in L1 can be used in order to allow the detection of a maximum of intensity of the current. This maximum indicates that the piezoelectric 5 vibrates at its resonance frequency. Indeed, as one already said, the impedance of a piezoelectric device reaches its minimum at the resonance frequency. Thus, at the resonance frequency, the load connected between the terminals of the secondary L2 is minimal. In such conditions, it can happen that the load is insufficient to completely dissipate the energy stored in the transformer. This situation is illustrated by the graphs of FIG. 3B. While referring to this graph, one can see that, when the load is particularly low, current IL2 and voltage UL2 do not have time to fall to zero before the end of a half cycle. Furthermore, the energy not dissipated in the secondary is found in the primary at the beginning of the following half cycle. This non dissipated energy is responsible for the appearence of a current IL1 in the primary winding L1 at the beginning of the half cycle (FIG. 3B). It will thus be understood that below a certain threshold, the lower the impedance is, the greater the intensity of current IL1 in the primary is. It is followed from there that a current IL1 of maximum intensity indicates that the transducer vibrates at resonance. The measurement of current IL1 through the resistances 39A and 39B can advantageously be used in a feedback loop (not shown) to drive the oscillator 27 so that it oscillates at the resonance frequency of the piezoelectric 5.

One can see on FIG. 2 that each of the transformers 11A and 11B further comprises a tertiary winding L3. The winding L3 of the transformer 11A is connected, in series with a diode 31 and one resistance 35, between the voltage source 17 and the ground. In a similar way, winding L3 of the transformer 11B is connected, in series with diode 33 and one resistance 37, between the source of voltage 17 and the ground. As one will see in more details hereafter, the function of the L3 winding is to limit the maximum power provided out of the secondary L2.

The speed with which the intensity of the current in L2 decreases when the energy stored in one of the transformers is transferred to the load naturally depends on the impedance associated with the load. Higher the impedance, faster the decrease of the current, and higher the voltage between the terminals of the secondary winding. The graphs of FIG. 3B describe the behaviour of the generator of FIG. 2 in a situation where the mechanical load on the piezoelectric transducer 5 is particularly high. One can see on FIG. 3B that the intensity of current IL2 decreases appreciably faster than in FIG. 3A. Moreover, voltage UL2 at the beginning of a half cycle is also considerably higher than in the case of FIG. 3A. It will be understood that if, for one reason or another, the mechanical load on the piezoelectric rises in an uncontrolled way, the output voltage of UL2 is likely to increase to the point of damaging the generator. This is why, in this example, each transformer 11A and 11B comprises a third winding L3 which is coupled inductively with the primary and secondary windings L1 and L2.

While referring again to FIG. 2, one sees that diodes 31 and 33 are connected to the winding L3 by their cathode, and to the ground by their anode. As the other terminal of each of the windings L3 is connected to the positive terminal of the voltage source 17, the diodes are normally subjected to a negative voltage UL3. In such conditions, diodes 31 and 33 prevent the passage of the current. However, if the voltage induced in L3 exceeds the continuous supply voltage, the resulting voltage UL3 on the diodes transitorily becomes positive, and a current IL3 starts to circulate in L3. This transitory current IL3 has the effect of limiting the voltage UL2 between the terminals of winding L2. The presence of the winding L3 thus allows to limit the voltage UL2 at a value which is determined by the choice of the relationship between the values of inductions L2 and L3.

Figure 1A:
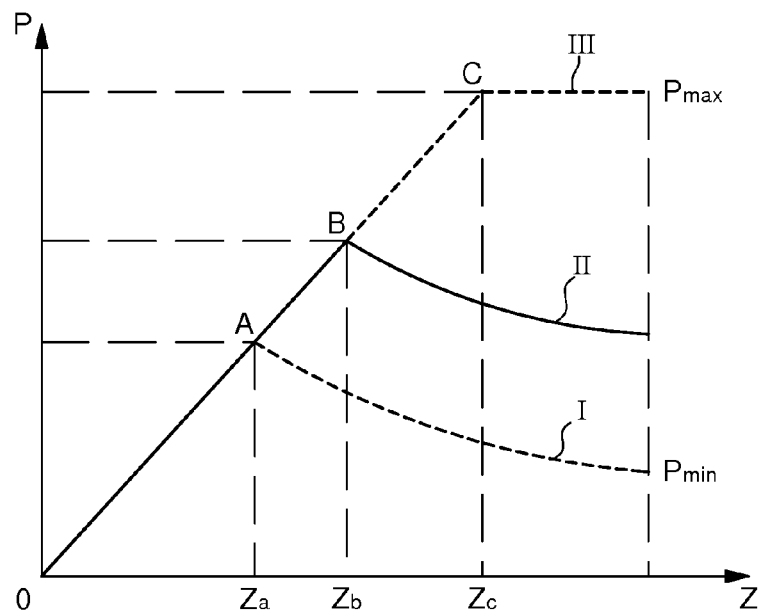
FIG. 1A is a graph of the power delivered by a prior art generator as a function of the impedance of the piezoelectric transducer.
Figure 1B:
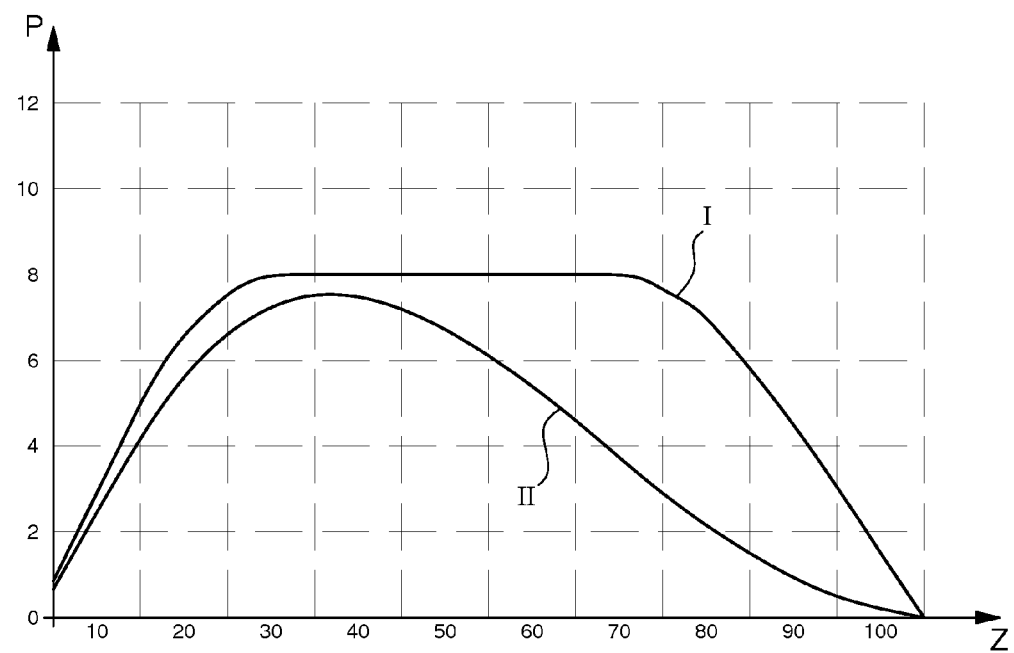
FIG. 1B is a graph allowing comparison of the power delivered by a generator according to the present invention with the power delivered by a prior art generator.
Figure 3C:
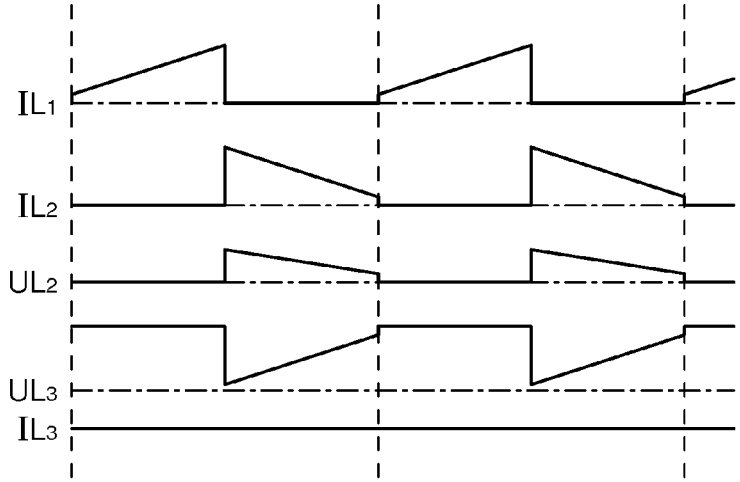

FIG. 1B is a graph comprising a first curve which shows the behaviour of the power provided by the generator which has just been described as a function of the impedance of the piezoelectric transducer. The graph also comprises a second curve which corresponds to the behaviour of a prior art generator like the one described in patent document FR 2'391'001 already mentioned. One sees on FIG. 1B that the first curve comprises a first increasing portion, a second constant portion and finally a third decreasing portion. The second portion occupies all the central part of the graph and thus corresponds to median values of the impedance. In this interval, the power provided by the generator according to the invention is appreciably constant, and the behaviour of the generator corresponds to what is described by the graphs of FIG. 3A. The first portion of the curve corresponds to values of the impedances which are not sufficient to entirely dissipate the energy stored in the transformers before the end of a half cycle. This first portion of the curve corresponds to an interval in which the behaviour of the generator is similar to what is described by the graphs of FIG. 3C. In this interval, the power supplied is reduced proportionally to the impedance. The third portion of the curve corresponds to the highest impedances. The behaviour of the generator in this zone corresponds to what is described by the graphs of FIG. 3B. In this zone, the voltage between the terminals of the secondary L2 y is limited by winding L3 and the current thus decreases as the impedance grows.

Another advantage of this invention is that the transformers 11A and 11B create a galvanic insulation between the piezoelectric transducer 5 and the power supply 17. On FIG. 2, the separation of the generator into two zones separated by a galvanic insulation, is represented by a rectangle in broken lines 40. One can further see on FIG. 2 that the switches 21A and 21B are inside the rectangle in broken line. To ensure the galvanic insulation at the level of the drive of the switches, an optocoupler 43 is inserted between oscillator 27 and one amplifier/inverter 45 designed to drive both switches.

What is claimed is:

1. A generator for a piezoelectric transducer comprising two transformers each including a primary winding and a secondary winding, and four switches driven by an ultrasonic frequency oscillator, two of said four switches being designed to connect alternately the secondary of each transformer to the piezoelectric load, and the two other switches being designed to connect alternately the two primary windings to a power supply so that during a first half cycle, called "the positive half cycle" the primary winding of one of said two transformers is charged with power, while the secondary winding of the other transformer discharges power to the piezoelectric load, and so that during a second half cycle, called "the negative half cycle" the secondary winding of said one transformer discharges power to the piezoelectric load, while the primary winding of the other transformer is charged with power.

2. The generator for a piezoelectric transducer according to claim 1, in which each transformer comprises a third winding maintained at a fixed voltage and a diode in series with the third winding so as to limit the negative voltage between the terminals of the third winding.

3. The generator for a piezoelectric transducer according to claim 1, in which at least one of the two transformers comprises a circuit for measuring the current in the primary winding for making it possible to monitor the shape of the current in such a way as to detect a possible trapezoidal shape of the current caused by the presence of non dissipated energy remaining from the preceding half-cycle.

4. The generator for a piezoelectric transducer according to claim 2, in which at least one of the two transformers comprises a circuit for measuring the current in the primary winding for making it possible to monitor the shape of the current in such a way as to detect a possible trapezoidal shape of the current caused by the presence of non dissipated energy remaining from the preceding half-cycle.

5. The generator for a piezoelectric transducer according to claim 2, in which at least one of the two transformers comprises an additional circuit for measuring the current in the third winding for making it possible to detect if a current runs through the third winding, and thus to detect if the negative voltage between the terminals of the third winding has been limited.

6. The generator for a piezoelectric transducer according to claim 4, in which at least one of the two transformers comprises an additional circuit for measuring the current in the third winding for making it possible to detect if a current runs through the third winding, and thus to detect if the negative voltage between the terminals of the third winding has been limited.

* * * * *